United States Patent [19]

Furler

[11] 4,369,794
[45] Jan. 25, 1983

[54] PROBE WITH ELECTROCARDIOGRAPHIC MONITORING

[75] Inventor: Alan G. Furler, Glens Falls, N.Y.

[73] Assignee: Mallinckrodt, Inc., St. Louis, Mo.

[21] Appl. No.: 202,119

[22] Filed: Oct. 30, 1980

[51] Int. Cl.³ ............................................... A61B 5/02
[52] U.S. Cl. ................................... 128/671; 128/642; 128/696; 128/715; 339/97 P
[58] Field of Search ............... 128/642, 670, 671, 696, 128/700, 736, 784–786, 419 P, 715, 773; 339/96, 97 P, 98, 99 R, 255 P, 261

[56] References Cited

U.S. PATENT DOCUMENTS

| | | | |
|---|---|---|---|
| 2,402,766 | 6/1946 | Moore | 339/98 |
| 2,408,045 | 9/1946 | Cottrell | 339/99 R |
| 3,242,256 | 3/1966 | Jugle | 339/98 X |
| 3,303,266 | 2/1967 | Thompson | 174/84 |
| 3,649,954 | 3/1972 | Kurtz | 339/255 P X |
| 3,861,771 | 1/1975 | Cornell | 339/95 |
| 3,868,165 | 2/1975 | Gonser | 339/97 R |
| 3,914,007 | 10/1975 | Seidler | 339/255 P |
| 3,924,639 | 12/1975 | Hess | 128/418 |
| 4,153,321 | 5/1979 | Pombrol | 339/261 X |
| 4,176,660 | 12/1979 | Mylrea et al. | 128/671 |

FOREIGN PATENT DOCUMENTS 665889  6/1979  U.S.S.R. ............................. 128/642

Primary Examiner—Lee S. Cohen
Attorney, Agent, or Firm—Bernard, Rothwell & Brown

[57] ABSTRACT

A tubular disposable probe, having a central lumen having a plurality of conductive pathways extending longitudinally of the probe from the proximal end to the distal end, and a reusable connector are provided. The reusable connector is formed of a resilient plastic material and includes two portions which are movable away from each other to permit installation of the connector on the probe at an appropriate point and are movable toward each other in clamping relationship to retain the connector on the probe wall. The connector includes a plurality of sharp prongs adapted to penetrate into the wall of the tube and make contact with the conductive pathways. The connector further includes projecting engageable elements for limiting the inward movement of the two portions of the connector so as to prevent any significant reduction in the size of the central lumen when the connector is installed. Alternatively, transverse grooves or notches are formed in the exterior wall of the tube and extend into the conductive pathways. In this case, the connector is formed with contacts conforming to the notches and receivable in the transverse notches for making connection with the conductive pathways in the probe.

10 Claims, 6 Drawing Figures

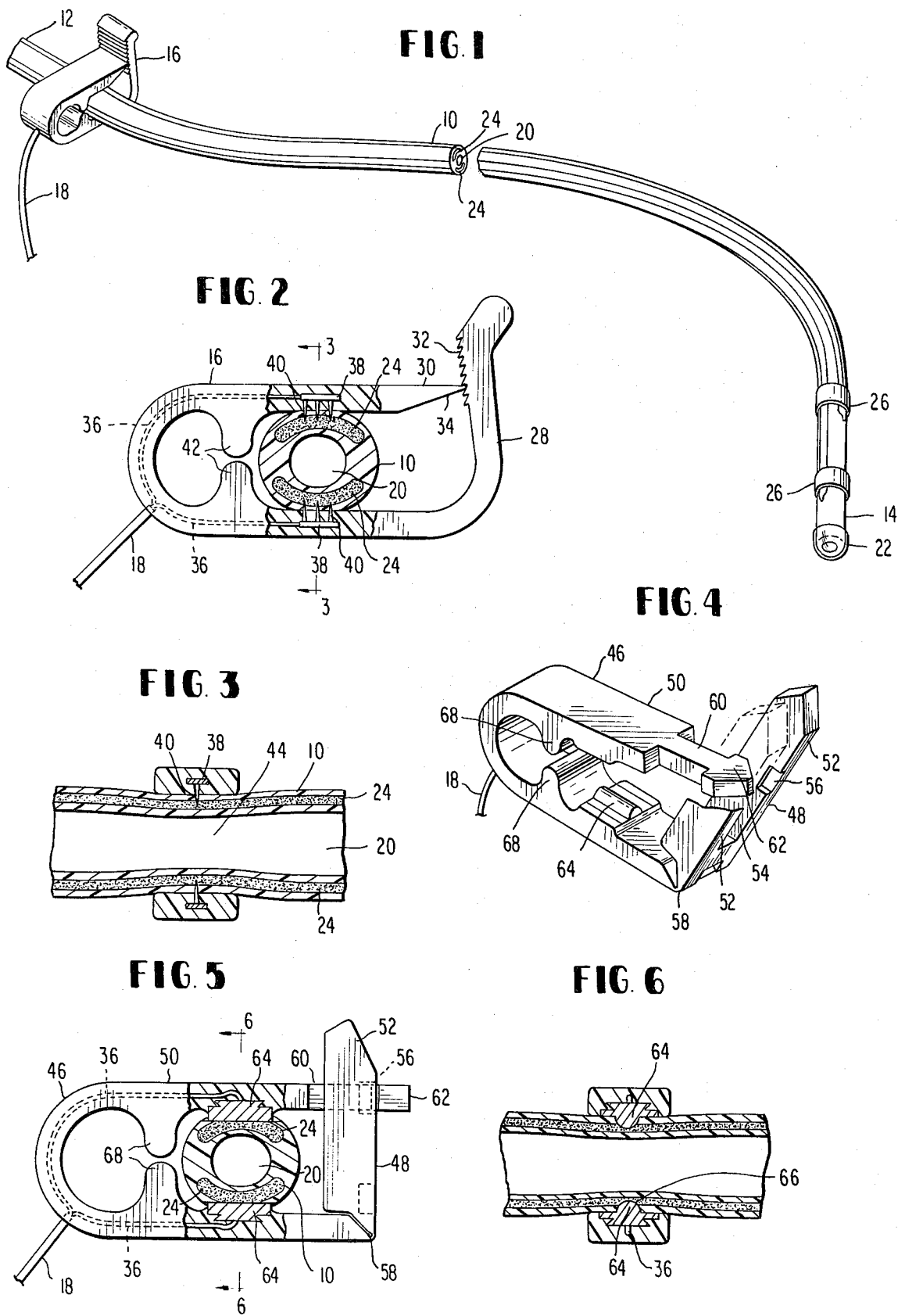

PROBE WITH ELECTROCARDIOGRAPHIC MONITORING

BACKGROUND OF THE INVENTION

1. Field of the Invention

This invention relates to probes for monitoring internal conditions of a patient and particularly to disposable esophageal probes including a reusable connector for electrocardiographic or other electrical signal monitoring.

2. Description of the Prior Art

In connection with operations or in intensive care units, it is sometimes necessary to employ an esophageal or a tracheal probe to monitor conditions internal of a patient. Such probes may include provision, for example, for detecting internal heart or lung sounds by means of a central passage in the probe or, in the case of tracheal probes, the central passage may provide for transmission of air. Such probes may include provision for supplying of a variety of other information concerning internal conditions. For example, the probe may include conductors or conductive passageways in the walls thereof for transmitting from the distal end of the probe electrical signals indicative of heart condition, that is, electrocardiographic signals. In addition, the probe may include provision for temperature sensing, including electrical conductors extending from a thermocouple, thermistor, or other suitable sensor at the distal end of the probe.

In the case of electrocardiographic signals, for example, it is necessary to provide a connection from the probe to an electrocardiographic recording instrument for conducting the electrical signals from the probe to the instrument. Particularly in the case where, as is increasingly the situation, it is desired to make the probe itself disposable, it is desirable that provision be made for a reliable and relatively simple connection to the probe for such electrocardiographic monitoring.

Various approaches have been employed for providing a detachable connection between the conductors carrying the electrocardiographic signals in the probe and the electrocardiographic monitoring instrument. For example, in one such arrangement, shown in U.S. Pat. No. 4,176,660-Mylrea et al., a plurality of longitudinally extending conductive pathways are provided in the wall of the tubular probe and a connector having a corresponding plurality of longitudinally extending prongs is provided for insertion into the disposable probe to make the electrical connection between the prongs and the several conductive pathways. In structures of this type, however, it requires very careful alignment of the prongs with the conductive pathways in the disposable probe to insure that the proper and effective connections are made between the two. Further, in such structures it may be necessary to interrupt the connection between the central passageway of the probe and an external component when the electrical connection is interrupted, and this may not be desirable, particularly when a tracheal probe is involved.

Resilient clamps of various types have been employed as a convenient means of pinching shut plastic tubing, including that used in medical procedures. Such clamps may be formed of a resilient plastic material and may include a recess in one position engageable by a tongue on another portion to hold the clamp releasably in its tub-pinching position. Such clamps have not been employed, however, insofar as the applicant is aware, for making electrical connections. The applicant has modified clamps of this general type to make them suitable as reusable connectors for establishing electrical contact with conductive elements in a disposable probe and conveying electrical signals therefrom to suitable monitoring instruments. Further, the clamps of the applicant's invention can be applied to the probe and removed from the probe without interrupting the continuity between the central passageway or lumen of the probe and any external component to which it is connected.

Thus, in accordance with the present invention, a disposable probe and a reusable connector suitable for connection to the disposable probe are provided, and the connector is constructed so that it may be easily placed on the probe and removed from the probe. Further, the connector as constructed insures reliable and effective electrical connections, can be installed without the need of critically careful alignment of the connector with the probe, and will make effective electrical contact without any risk of significantly pinching or reducing the size of a central passageway or lumen of the probe. Finally, the connector may be connected and disconnected electrically without affecting the continuity of connections to the central lumen of the probe.

Accordingly, it is an object of this invention to provide a probe, for example a disposable esophageal or tracheal probe, and an effective, relatively inexpensive and reliable reusable connector for providing electrical connection between the probe and any suitable monitoring instrument.

It is another object of this invention to provide the probe of the above types in which the connector can make effective electrical contact, but without any risk, of significantly reducing the size of the central lumen in the probe.

It is a further object of this invention to provide an arrangement in which the connector may be connected in and disconnected from electrical contact with the probe without affecting continuity between the probe lumen and any device to which it is connected.

SUMMARY OF THE INVENTION

In carrying out the invention, in one form thereof, a disposable probe is provided which includes a tube of any suitable material, such as polyvinyl chloride, having a plurality of conductors or conductive pathways extending longitudinally of the tubular probe from the proximal to the distal end within the tubular wall of the probe. The probe includes a central open passageway or lumen which may provide for the conducting of sound therethrough to a stethoscope connected to the proximal end thereof or, in the case of a tracheal probe, may provide for the passage of air to and from the lungs. In order to provide for transmission of electrical signals from the disposable probe to a monitoring instrument, such as an electrocardiographic monitor, a reusable connector is provided, in accordance with this invention, for connecting the instrument to the conductive pathways in the probe wall. The connector is preferably formed of a resilient plastic material and includes two portions which are movable away from each other to permit installation of the connector on the probe at an appropriate point and are movable toward each other in clamping relationship to retain the connector on the probe wall. The connector includes, in one form of the invention, a plurality of sharp prongs adapted to penetrate into the wall of the tube and make contact with the conductive pathways. The connector further includes projecting engageable elements for limiting the inward movement of the two portions of the connector so as to prevent any significant reduction in the size of the central lumen of the probe when the connector is installed. In another form of the invention, transverse grooves or notches are formed in the exterior wall of the tube and extend into the conductive pathways. In this case, the connector is formed with conductive surfaces conforming to the notches and receivable in the transverse notches for making connection with the conductive pathways in the disposable probe.

BRIEF DESCRIPTION OF THE DRAWINGS

In the following description, reference is made to the accompanying drawings in which:

FIG. 1 is a perspective view of a disposable probe and connector constructed in accordance with this invention;

FIG. 2 is an enlarged sectional view of the connector shown in FIG. 1;

FIG. 3 is a sectional view taken along the line 3—3 in FIG. 2;

FIG. 4 is a perspective view of a modified form of a connector;

FIG. 5 is a view, partly in section, of the connector of FIG. 4 in its assembled position on the disposable probe; and FIG. 6 is a sectional view taken along the line 6—6 in FIG. 5.

DESCRIPTION OF THE PREFERRED EMBODIMENTS

Referring to FIG. 1 there is shown one embodiment of the disposable probe and connector arrangement of this invention. As there shown, the device includes a disposable probe 10 having a proximal end 12 and a distal end 14. The probe is intended to be inserted into the human body, for example, in connection with surgical procedures or for monitoring in an intensive care unit. The particular probe illustrated in FIG. 1 is an esophageal probe, but it will be apparent as the description proceeds that the device is suitable, with appropriate modification, for other internal uses. The device of this invention further includes a reusable connector 16 which is adapted to be removably mounted on the disposable probe and which includes an electrical lead 18 which may be connected to any suitable monitoring instrument, for example, an electrocardiographic monitoring instrument (not shown).

The probe, in the form shown, is a flexible tubular member, preferably formed from a suitable plastic material such as polyvinyl chloride. The tubular member includes a major central lumen 20 which extends the full length of the tubular member from the proximal end to the distal end thereof. In the form shown, the distal end is closed by a membrane 22 and it is contemplated that this portion of the probe will be employed for monitoring heart or lung sounds, such acoustic information being transmitted through the lumen 20 to a stethoscope or other suitable monitoring instrument (not shown) which may be connected to the proximal end of the probe. In the case of a tracheal probe, the member 22 would be omitted and the distal end of the probe would be left open for transmission of fluid to and from the body. Formed within the probe and extending substantially the full length of the probe are a plurality of circumferentially spaced electrically conductive pathways 24. These pathways may be formed, for example, of a polyvinyl material impregnated with electrically conductive particles of carbon or other suitable conductive materials. The pathways may be formed in a conventional manner by extruding such pathways simultaneously with the extrusion of the tubular probe itself. Spaced electrodes 26 are formed along the exterior of the probe near the distal end thereof. One of the conductive pathways 24 is connected to one of the electrodes 26 and the other pathway 24 is connected to the other of the electrodes 26. Signals indicative of heart condition are developed at the electrodes 26 and transmitted through the pathways 24 to the connector 16 and through the lead 18 to an electrocardiographic monitoring instrument.

In accordance with the present invention, a simple and effective arrangement is provided for establishing connection, when desired, with the conductive pathways 24 and communicating the electrical signals in these conductive pathways to a suitable monitoring instrument. Referring now to FIGS. 2 and 3, in addition to FIG. 1, the connector 16 is formed of a resilient material and preferably of a resilient plastic material, such as terpolymer of acrylonitrile-butadiene-styrene (ABS), polycarbonate, polyethylene or polypropylene. The connector is made in somewhat loop form and includes a first portion 28 and a second portion 30 which are biased toward each other by the resiliency of the material of which the connector is formed. In the form shown in FIG. 2, the first portion 28 includes on its inner surface, a plurality of serrations 32 and the second portion 30 is formed with a relatively sharp edge 34 which is positioned to engage any selected one of the serrations 32. It will be apparent from reference to FIG. 2 that the edge 34 will be brought into engagement with one or another of the serrations 32 depending on the size of the tubular probe with which the connector is used. Once the edge 34 has been brought into engagement with the appropriate serration the two parts are retained in engagement by the resilience of the material of which the connector is formed.

Conductors 36 extending from the lead 18 are embedded within the plastic material of which the connector 16 is formed and each of these connectors is connected in electrical engagement with a corresponding one of two contacts 38 which are also embedded in the plastic material. Each contact 38 includes one or more prongs 40 extending inwardly through the inner wall of the connector and projecting a short distance beyond the inner wall. The conductors 36 and the contacts 38 may be fabricated contemporaneously with the connector 16 by an insert molding process well known in the art. In that form shown in FIG. 2, each contact 38 includes three prongs 40, but it will be apparent that more or fewer prongs can be employed if desired. Each of the prongs 40 has a relatively sharp point at the inner end so as to facilitate penetration of the wall of the probe 10 to establish conducting engagement with corresponding one of the conductive pathways 24.

It will be apparent from FIG. 2 that the portions 28 and 30 of the connector 16 may be moved away from each other against the bias of the resilience of the connector to provide an opening therebetween sufficiently large to allow the connector to be slipped over the disposable probe 10. The two portions 28 and 30 are then moved toward each other so that the prongs 40 penetrate the wall of the probe 10 and move into electrical contact with the conductive pathways 24. Whether the probe is used as an esophageal probe or a tracheal probe, it is undesirable that any significant constriction of the lumen 20 be permitted when the connector 16 is placed on the probe and the prongs 40 are caused to penetrate the wall thereof and to contact the conductive pathways 24. In order to limit the inward movement of the contacts 38 and prongs 40 as this engagement with the conductive passageways is effected, the connector 16 is formed to include two inwardly extending aligned projections 42. These projections are of sufficient size that they engage each other and prevent further inward movement of the two relatively movable portions of the connector after the prongs 40 have penetrated sufficiently into the conductive pathways 24 to establish good electrical contact. At that point, the sharp edge 34 will be brought into engagement with the appropriate one of the serrations 32 to hold the clamp in that position, the sharp edge 34 being biased against the engaged serration by the resilience of the connector 16 and the resilience of the slightly compressed wall of the probe 10. The connector therefore remains in fixed engagement with the disposable probe 10 until it is removed after the disposable probe has served its purpose.

Referring to FIG. 3, it can be seen that the wall of the probe is slightly compressed by the connector in its assembled position so that there is a slight constriction in the lumen 20 in the area 44 where the connector is positioned. However, the amount of this constriction, because of the limitation imposed by the projections 42, is limited and does not interfere with the function performed by the lumen 20, whether it be employed for conducting sound, as in an esophageal probe, or conducting fluid, as in a tracheal probe. While in the form of the invention shown, two aligned projections 42 of the same size are employed, it will be apparent that they could be of different sizes or, if desired, a single larger projection, extending inwardly from one portion and engaging the other portion, could be employed. The only requirement is that the combined size of two projections, or the size of a single projection, be such as to limit inward movement of the two portions of the connector so that no significant reduction in the size of the lumen occurs. The connector 16 can be effectively assembled on the probe 10 to serve its purpose of conducting even low voltage electrical signals to a monitoring instrument without interfering in any way with other functions performed by the probe through the lumen 20. Moreover, the connector can be assembled to the probe 10 and disconnected therefrom without affecting in any way the continuity of the probe extending from the distal to the proximal end. Thus, any function performed by the lumen 20 is no way affected by the assembly of the connector on the probe or the disassembly of the connector from the probe.

Moreover, the connector can be assembled in appropriate electrical engagement with the conductive pathways 24 without any need for very careful alignment of the connector and the probe. In the form shown, the conductive pathways 24 are of arcuate form and extend a significant distance circumferentially of the wall of the probe 10. As can be readily seen from FIG. 2 there can be a substantial angular variation in the position of the connector 16 while still insuring that all, or at least some, of the prongs establish electrical contact with the conductive pathways 24. In some cases the probe is formed of transparent plastic material so that the pathways 24 are clearly visible and the connector may be easily assembled in the appropriate position. If the probe is made of an opaque material, or to identify the conductive pathway associated with a particular electrode, an indicating line or other mark can be easily placed on the exterior of the probe opposite each of the pathways 24 to facilitate easy positioning of the connector at the appropriate angular location on the probe. It will be apparent that there is a relatively wide range of positions in which the connector may be assembled and still serve its function so that no precise care need be employed in assembling the conductor on the probe.

While in the particular form shown only two conductive pathways have been employed it will be apparent that a greater number of such pathways, circumferentially spaced about the wall of the probe, could be employed if it were desired to provide additional paths for electrical signals monitoring other conditions at the distal end of the probe. This would, of course, involve providing additional spaced prongs on the inner walls of the connector to establish contact with these additional pathways and would reduce the amount of angular variation permitted in proper assembly of the connector on the probe. However, even if, for example, two additional conductive pathways were employed the construction provided by this invention would still eliminate the need for any extremely precise positioning of the connector on the probe. Further, if desired, minor lumens could be provided in the wall of the probe intermediate the conductive pathways and electrical conductors could be extended through these minor lumens to the distal end and connected, for example to a temperature-sensing thermocouple, thermistor, or other suitable sensor, at the distal end, providing additional information without interfering with the functioning of the connector.

A modified form of connector usable in this invention is shown in FIGS. 4-6. Similarly to the form of connector just described, the connector 26 shown in FIGS. 4-6 is also formed from a resilient material and preferably a resilient plastic material such as terpolymer of acrylonitrile-butadiene-styrene (ABS), polycarbonate, polyethylene or polypropylene. It also includes two relatively movable portions 48 and 50. However, the manner of engaging these portions is somewhat different. In the form shown in FIGS. 4-6, the portion 48 is formed to include two spaced arms 52 defining a slot 54 therebetween. Recesses, one of which is shown at 56, are formed on the inner wall of each of the arms 52. The arms 52 are hingedly connected at 58 to the first portion 50 of the connector 46. The portion 50 includes a tongue 60 which is adapted to be received in the slot 54, and it further includes an enlarged head 62 which, in the assembled position of the clamp, is receivable in the recesses 56. The hinge connection 58 permits the portion 48 to be moved outwardly relative to the portion 50 to provide an opening between the two portions for assembly of the connector on the disposable probe. After the connector has been assembled on the probe the hinged portion 48 is moved toward the position shown in FIG. 5 and the tongue 60 of the portion 50 is moved downwardly through the slot 54 until the head 62 is aligned with the recesses 56. The resilience of the connector then causes the head 62 to be pulled into engagement with the recesses 56 to hold the clamp in its assembled position.

As in the form of invention shown in FIGS. 1-3, the connector 46 includes conductors 36 extending from lead 18 and embedded in the plastic of which the connector 46 is formed. These conductors 36 extend to contacts 64 which are formed on opposing inner surfaces of the connector 46. As shown best in FIG. 6 the contacts 64 are preferably formed in a U-shaped cross section extending longitudinally of the connector, but they may also be formed in other shapes, for example, in a V-shaped cross section. The contacts 64 are formed of conductive material and are connected in electrical contact with the conductors 36. In this form of the invention, the disposable probe is formed to provide two circumferentially spaced grooves or notches 66 at opposite sides of the probe 10. These notches are of sufficient depth to penetrate through the plastic wall of the probe and into the conducting pathways 24. These notches are preferably of U-shaped cross section but may be of other shapes, for example, V-shaped cross section. It can be seen that when the connector 46 is assembled on the probe and the portions 48 and 50 are brought into engagement as previously described, the contacts 64 are received within the notches 66 and make good electrical contact with the conductive pathways 24.

As in the case of the form of invention shown in FIGS. 1-3, the connector 46 includes two aligned inwardly extending projections 68. Like the projections 42 of the connector 16 these projections 68 extend inwardly a sufficient distance so that they will engage each other to limit relative inward movement of the portions of the connector to an extent that no significant reduction in the size of the lumen 20 can occur. While two inwardly extending projections 68, both extending inwardly from the corresponding wall of the connector by the same amount, have been shown, it will be apparent that, if desired, a single projection extending from one wall could be employed, this projection being of sufficient length to engage the opposite wall of the connector and limit the inward movement of the relatively movable portions of the connector so that no significant restriction of the lumen 20 can occur. Also, while the two projections 42 have been shown as of equal size, and this is the preferred construction, the projections could be made of different sizes so long as the combined size of the two projections provides the required limitation on inward movement of the two portions of the connector.

As in the case of the form of invention shown in FIGS. 1-3, the form of invention shown in FIGS. 4-6 may employ a suitable indicating mark or tab placed on the exterior of the wall of the probe to indicate the appropriate location for the connector 46. However, the notches 66 are easily visible from the exterior of the probe and themselves provide a completely satisfactory means of locating the connector at the proper angular position on the probe.

While the specific embodiments of this invention have been shown and described, it will be apparent that modifications could be made without departing from the invention, and it is intended by the appended claims to cover all such modifications as come within the spirit and scope of this invention.

It is claimed:

1. A disposable probe for monitoring internal conditions of a patient and a reusable connector for use with said probe, comprising:
   (a) a tubular member having a central lumen and having a proximal portion and a distal portion, said distal portion being adapted to be inserted internally of the patient, and including means for electrically monitoring an internal condition of the patient;
   (b) said tubular member including a plurality of circumferentially spaced conductive pathways in the wall thereof extending between said proximal portion and said monitoring means for conducting electrical signals;
   (c) a connector mountable on said proximal portion in a position extending transversely of said tubular member;
   (d) said connector including a plurality of spaced members each electrically engaging a corresponding one of said conductive pathways and including conductors connected to said members and extending externally of said connector for attachment to suitable monitoring apparatus for conveying said signals to the apparatus;
   (e) said connector including relatively movable first and second sections positively holding said connector in clamping engagement with said tubular member and holding said engaging members in electrical contact with said conductive pathways;
   (f) said connector including means for limiting clamping movement of said sections to prevent constriction of said lumen by said connector.

2. The probe and connector of claim 1 wherein said means for limiting clamping movement comprises an inwardly extending projection on at least one of said sections, said projection being positioned to engage the other of said sections.

3. The probe and connector of claim 1 wherein said means for limiting clamping movement comprises:
   (a) a first inwardly extending projection on said first section;
   (b) a second inwardly extending projection on said second section aligned with said first projection;
   (c) said projections being positioned to abut each other to limit relative inward movement of said sections.

4. The probe and connector of claim 1 wherein one of said sections includes a recess and the other of said sections includes a member engaging said recess to hold said connector in position engaging said tubular member.

5. The probe and connector of claim 1 wherein each of said spaced members of said connector includes an inwardly extending prong, each of said prongs penetrating the wall of said tubular member to make electrical contact with a corresponding one of said pathways when said connector is in its clamping position.

6. The probe and connector of claim 1 wherein:
   (a) said conductive pathways are of arcuate cross section; and
   (b) each of said spaced members of said connector includes a set of inwardly extending prongs, each of said sets including a plurality of prongs displaced from each other circumferentially of said connector and transversely of said tubular member, the prongs of one of said sets penetrating the wall of said tubular member to make electrical contact with one of said pathways when said connector is in its clamping position and the prongs of the other of said sets penetrating the wall of said tubular member to make electrical contact with the other of said pathways when said connector is in its clamping position.

7. The probe and connector of claim 1 wherein:

(a) said tubular member has a plurality of circumferentially spaced grooves in the exterior of said wall thereof, each of said grooves being of sufficient depth to expose a corresponding conductive pathway; and
(b) each of said sections includes a conducting member received in a corresponding one of said grooves making electrical contact with a corresponding one of said pathways.

8. The probe and connector of claim 7 wherein each of said grooves comprises a substantially U-shaped notch extending transversely of said tubular member and each of said conducting members includes an element of substantially U-shaped cross section received in a corresponding one of said notches.

9. The probe and connector of claim 1 wherein said connector is formed of a resilient plastic material.

10. The probe and connector of claim 1 wherein said conductive pathways are of arcuate cross section to permit greater flexibility in alignment of said connector with said probe.

* * * * *